United States Patent [19]
Sandal et al.

[11] Patent Number: 5,827,719
[45] Date of Patent: Oct. 27, 1998

[54] ENZYME WITH LIPOLYTIC ACTIVITY

[75] Inventors: Thomas Sandal; Sakari Kauppinen, both of Copenhagen N; Lene Venke Kofod, Uggerløse, all of Denmark

[73] Assignee: Novo Nordisk A/S, Bagsvaerd, Denmark

[21] Appl. No.: 817,997

[22] PCT Filed: Oct. 26, 1995

[86] PCT No.: PCT/DK95/00427

§ 371 Date: Apr. 25, 1997

§ 102(e) Date: Apr. 25, 1997

[87] PCT Pub. No.: WO96/13580

PCT Pub. Date: May 9, 1996

[30] Foreign Application Priority Data

Oct. 26, 1994 [DK] Denmark ................. 1240/94

[51] Int. Cl.⁶ ............. C12N 1/15; C12N 15/55; C12N 15/63; C12P 21/02
[52] U.S. Cl. .......... 435/198; 435/254.3; 435/254.6; 435/320.1; 435/325; 536/23.2
[58] Field of Search ................. 435/320.1, 325, 435/252.3, 254.11, 198, 254.3, 254.6; 536/23.2; 510/392

[56] References Cited

U.S. PATENT DOCUMENTS 4,810,414  3/1989  Huge-Jensen et al. ............. 510/320
5,466,594  11/1995 Outtrup et al. ................... 510/320
5,601,978  2/1997  Burczak et al. ................... 435/6

FOREIGN PATENT DOCUMENTS 305216    3/1989  European Pat. Off.
WO 93/11249  6/1993  WIPO.

*Primary Examiner*—Eric Grimes
*Attorney, Agent, or Firm*—Steve T. Zelson, Esq.; Valeta Gregg, Esq.

[57] ABSTRACT

The invention relates, inter alia, to a DNA construct comprising a DNA sequence which encodes an enzyme exhibiting lipolytic activity and which comprises: a) the DNA sequence shown in SEQ ID No. 1, or b) an analogue of the DNA sequence shown in SEQ ID No. 1 which i) is homologous with the DNA sequence shown in SEQ ID No. 1, and/or ii) hybridizes with the same oligonucleotide probe as the DNA sequence shown in SEQ ID No. 1, and/or iii) encodes a polypeptide which is homologous with the polypeptide encoded by a DNA sequence comprising the DNA sequence shown in SEQ ID No. 1, and/or iv) encodes a polypeptide which is immunologically reactive with an antibody raised against a purified lipolytic enzyme which is encoded by the DNA sequence shown in SEQ ID No. 1 and/or which is derived from *Humicola insolens* DSM 1800. Also disclosed, inter alia, are: lipolytic enzymes encoded by such DNA constructs; and enzyme preparations, detergent additives and detergent compositions comprising such lipolytic enzymes.

11 Claims, 1 Drawing Sheet

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 994 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Coding Sequence
        ( B ) LOCATION: 43...729
        ( D ) OTHER INFORMATION:

( x i ) SEQUENCE DESCRIPTION: SEQ ID NO:1:

```
GCCACCACTT  ACCAACCAGC  TTCCGCAAAC  AAAGTCGCCA  AC  ATG  AAG  TTC  TTC                54
                                                    Met  Lys  Phe  Phe
                                                    -35

ACC  ACC  ATC  CTC  AGC  ACC  GCC  AGC  CTT  GTT  GCT  GCT  CTC  CCC  GCC  GCT       102
Thr  Thr  Ile  Leu  Ser  Thr  Ala  Ser  Leu  Val  Ala  Ala  Leu  Pro  Ala  Ala
     -30                      -25                      -20

GTT  GAC  TCG  AAC  CAT  ACC  CCG  GCC  GCT  CCT  GAA  CTT  GTT  GCC  CGG  CAG       150
Val  Asp  Ser  Asn  His  Thr  Pro  Ala  Ala  Pro  Glu  Leu  Val  Ala  Arg  Gln
-15                      -10                      -5                           1

CTG  GGA  GCC  ATC  GAG  AAC  GGC  CTT  GAG  AGC  GGC  AGC  GCC  AAC  GCC  TGC       198
Leu  Gly  Ala  Ile  Glu  Asn  Gly  Leu  Glu  Ser  Gly  Ser  Ala  Asn  Ala  Cys
               5                      10                      15

CCC  GAC  GCC  ATC  CTG  ATC  TTT  GCT  CGC  GGC  TCG  ACC  GAG  CCA  GGC  AAC       246
Pro  Asp  Ala  Ile  Leu  Ile  Phe  Ala  Arg  Gly  Ser  Thr  Glu  Pro  Gly  Asn
               20                     25                     30

ATG  GGC  ATC  ACC  GTC  GGC  CCT  GCT  CTC  GCC  AAC  GGC  CTT  GAG  TCC  CAC       294
Met  Gly  Ile  Thr  Val  Gly  Pro  Ala  Leu  Ala  Asn  Gly  Leu  Glu  Ser  His
          35                          40                       45

ATC  CGG  AAC  ATC  TGG  ATC  CAG  GGC  GTC  GGC  GGC  CCT  TAC  GAC  GCC  GCG       342
Ile  Arg  Asn  Ile  Trp  Ile  Gln  Gly  Val  Gly  Gly  Pro  Tyr  Asp  Ala  Ala
50                       55                      60                          65
```

```
CTG GCC ACC AAC TTC CTG CCG CGG GGC ACC TCG CAG GCC AAC ATC GAC      390
Leu Ala Thr Asn Phe Leu Pro Arg Gly Thr Ser Gln Ala Asn Ile Asp
                 70                  75                  80

GAG GGC AAG CGG CTG TTT GCG CTG GCC AAC CAA AAG TGC CCC AAC ACG      438
Glu Gly Lys Arg Leu Phe Ala Leu Ala Asn Gln Lys Cys Pro Asn Thr
             85                  90                  95

CCC GTC GTC GCC GGC GGG TAC AGC CAG GGC GCG GCG CTC ATC GCT GCC      486
Pro Val Val Ala Gly Gly Tyr Ser Gln Gly Ala Ala Leu Ile Ala Ala
            100                 105                 110

GCC GTC AGC GAG CTC AGC GGC GCC GTC AAG GAG CAG GTC AAG GGC GTC      534
Ala Val Ser Glu Leu Ser Gly Ala Val Lys Glu Gln Val Lys Gly Val
        115                 120                 125

GCC CTC TTC GGA TAC ACC CAA AAC CTC CAG AAC CGT GGC GGC ATC CCC      582
Ala Leu Phe Gly Tyr Thr Gln Asn Leu Gln Asn Arg Gly Gly Ile Pro
130                 135                 140                 145

AAC TAC CCG CGC GAG CGC ACC AAG GTG TTC TGC AAC GTT GGC GAC GCC      630
Asn Tyr Pro Arg Glu Arg Thr Lys Val Phe Cys Asn Val Gly Asp Ala
                150                 155                 160

GTC TGC ACC GGC ACG CTC ATC ATC ACC CCG GCG CAT CTG TCG TAC ACG      678
Val Cys Thr Gly Thr Leu Ile Ile Thr Pro Ala His Leu Ser Tyr Thr
            165                 170                 175

ATC GAG GCG CGC GGT GAG GCC GCG AGG TTC CTG CGG GAT CGC ATC CGT      726
Ile Glu Ala Arg Gly Glu Ala Ala Arg Phe Leu Arg Asp Arg Ile Arg
        180                 185                 190

GCT TAAATGGAAT GGGTTATCAG AGGGAAAGAT GGCTGGATAG GTAACAAAGG           779
Ala

ATGAGTCCGG GCGGGATTGG GTTCAGGAGT TGGGCAGGCG GATTGCTCGA TGGCTGGATG    839

GATGGATGGA AGCCGGGCTG GGACCGGAGG CTGATGACGG TGATGACCTT TTTCCTCAGT    899

ACATAGCATC ATGATGTCTC CTGCACATAT CTGTTTATGA ATCGAGTTTT GGTTTGCGGC    959

CGCTGCCTCA GAAAAAAAAA AAAAAAAAAA AAAAA                              994
```

( 2 ) INFORMATION FOR SEQ ID NO:2:

( i ) SEQUENCE CHARACTERISTICS:
        ( A ) LENGTH: 229 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:2:

```
Met Lys Phe Phe Thr Thr Ile Leu Ser Thr Ala Ser Leu Val Ala Ala
-35             -30                 -25                 -20

Leu Pro Ala Ala Val Asp Ser Asn His Thr Pro Ala Ala Pro Glu Leu
            -15                 -10                 -5

Val Ala Arg Gln Leu Gly Ala Ile Glu Asn Gly Leu Glu Ser Gly Ser
             1                   5                  10

Ala Asn Ala Cys Pro Asp Ala Ile Leu Ile Phe Ala Arg Gly Ser Thr
            15                  20                  25

Glu Pro Gly Asn Met Gly Ile Thr Val Gly Pro Ala Leu Ala Asn Gly
30                  35                  40                  45

Leu Glu Ser His Ile Arg Asn Ile Trp Ile Gln Gly Val Gly Gly Pro
            50                  55                  60

Tyr Asp Ala Ala Leu Ala Thr Asn Phe Leu Pro Arg Gly Thr Ser Gln
            65                  70                  75
```

```
Ala Asn Ile Asp Glu Gly Lys Arg Leu Phe Ala Leu Ala Asn Gln Lys
        80              85              90

Cys Pro Asn Thr Pro Val Val Ala Gly Gly Tyr Ser Gln Gly Ala Ala
    95              100             105

Leu Ile Ala Ala Ala Val Ser Glu Leu Ser Gly Ala Val Lys Glu Gln
110             115             120                         125

Val Lys Gly Val Ala Leu Phe Gly Tyr Thr Gln Asn Leu Gln Asn Arg
                130             135                     140

Gly Gly Ile Pro Asn Tyr Pro Arg Glu Arg Thr Lys Val Phe Cys Asn
            145             150             155

Val Gly Asp Ala Val Cys Thr Gly Thr Leu Ile Ile Thr Pro Ala His
        160             165             170

Leu Ser Tyr Thr Ile Glu Ala Arg Gly Glu Ala Ala Arg Phe Leu Arg
    175             180             185

Asp Arg Ile Arg Ala
190
```

( 2 ) INFORMATION FOR SEQ ID NO:3:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

```
Gln Leu Gly Ala Ile Glu Asn Gly Leu Glu Ser Gly Ala Ser Ala Asn
1               5               10                      15

Ala Xaa Pro Asp Ala Ile Leu Ile Phe Ala Arg Gly
        20              25
```

# ENZYME WITH LIPOLYTIC ACTIVITY

CROSS-REFERENCE TO RELATED APPLICATIONS

This application is a 35 U.S.C. 371 national application of PCT/DK95/00427 filed Oct. 26, 1995 and claims priority under 35 U.S.C. 119 of Danish application 1240/94 filed Oct. 26, 1994, the contents of which are fully incorporated herein by reference.

FIELD OF THE INVENTION

The present invention relates to an enzyme with lipolytic activity, a DNA construct comprising a DNA sequence encoding the enzyme, and a method of producing the enzyme. The invention further relates, inter alia, to enzyme preparations, detergent additives and detergent compositions containing the enzyme, and to the use of the enzyme for a number of industrial and domestic applications.

BACKGROUND OF THE INVENTION

Although numerous lipolytic enzymes (enzymes which catalyze the hydrolysis of lipids, such as triglycerides) have been described and characterized in the literature, there is an continuing need for providing novel lipolytic enzymes, preferably in single-component form, having properties which improve their usefulness in various industrial or domestic applications, such as in detergent compositions for laundry washing or dishwashing, or compositions for hard-surface cleaning, degreasing/defatting and the like.

SUMMARY OF THE INVENTION

The present inventors have now surprisingly succeeded in isolating and characterizing a DNA sequence from a strain of *Humicola insolens*, which sequence encodes an enzyme exhibiting lipolytic activity, thereby making it possible to prepare a single-component lipolytic enzyme. Lipolytic enzymes of the invention have been found (vide infra) to possess properties which render them very well suited to, inter alia, a number of applications of the above-mentioned types.

Accordingly, in a first aspect the invention relates to a DNA construct comprising a DNA sequence encoding an enzyme exhibiting lipolytic activity, which DNA sequence comprises a) the DNA sequence shown in SEQ ID No. 1, and/or the DNA sequence encoding a lipolytic enzyme, which is obtainable from the plasmid in *Saccharomyces cerevisiae* DSM 9975, or b) an analogue of the DNA sequence shown in SEQ ID No. 1, and/or of the DNA sequence encoding a lipolytic enzyme, which is obtainable from the plasmid in *Saccharomyces cerevisiae* DSM 9975, which i) is homologous with the DNA sequence shown in SEQ ID No. 1 and/or the DNA sequence encoding a lipolytic enzyme, which is obtainable from the plasmid in *Saccharomyces cerevisiae* DSM 9975, and/or ii) hybridizes with the same oligonucleotide probe as the DNA sequence shown in SEQ ID No. 1, and/or the DNA sequence encoding a lipolytic enzyme, which is obtainable from the plasmid in *Saccharomyces cerevisiae* DSM 9975, and/or iii) encodes a polypeptide which is homologous with the polypeptide encoded by a DNA sequence comprising the DNA sequence shown in SEQ ID No. 1 and/or by the DNA sequence encoding a lipolytic enzyme, which is obtainable from the plasmid in *Saccharomyces cerevisiae* DSM 9975, and/or iv) encodes a polypeptide which is immunologically reactive with an antibody raised against a purified lipolytic enzyme which is encoded by the DNA sequence shown in SEQ ID No. 1 and/or by the DNA sequence encoding a lipolytic enzyme, which is obtainable from the plasmid in *Saccharomyces cerevisiae* DSM 9975, and/or which is derived from *Humicola insolens* DSM 1800.

It is believed that the DNA sequence shown in SEQ ID NO. 1 is identical to the DNA sequence encoding a lipolytic enzyme, which is obtainable from the plasmid in *Saccharomyces cerevisiae* DSM 9975.

The DNA sequence shown in SEQ ID NO 1 encodes the mature enzyme with its native signal peptide. Analogously, the amino acid sequence shown in SEQ ID NO 2 constitutes the mature enzyme (amino acids 36–246) with its signal peptide (amino acids 1–35).

It is to be understood that whenever reference is made to "the DNA sequence shown in SEQ ID NO 1 " in connection with the enzyme or DNA construct of the invention (e.g. as used in the above sections a) and b) i)-iv)), said sequence may be the entire sequence shown in SEQ ID NO 1, but is more preferably the part of the sequence which encodes the mature lipolytic enzyme.

Correspondingly, whenever reference is made to "the amino acid sequence shown in SEQ ID NO 2" in connection with the enzyme or DNA construct of the invention, it is to be understood that said sequence may be the entire sequence shown in SEQ ID NO 2, but is more preferably the part of the sequence constituting the mature lipolytic enzyme (i.e. amino acid residues 36–246).

In the present context, the "analogue" of the DNA sequence shown in SEQ ID No. 1 is intended to indicate any DNA sequence which encodes an enzyme exhibiting lipolytic activity, and which has one or more, or all, of the properties i)-iv). Such an analogous DNA sequence may be isolated from another or related (e.g. the same) organism producing the enzyme with lipolytic activity on the basis of the DNA sequence shown in SEQ ID No. 1 or a suitable subsequence (such as 20–500 bp) thereof, e.g. using the procedures described herein, and thus, e.g., be an allelic or species variant of the DNA sequence comprising the DNA sequence shown herein, or be constructed on the basis of the DNA sequence shown in SEQ ID No. 1, e.g. by introduction of nucleotide substitutions which do not give rise to another amino acid sequence of the lipolytic enzyme encoded by the DNA sequence, but which correspond to the codon usage of the host organism intended for production of the enzyme, or by introduction of nucleotide substitutions which may give rise to a different amino acid sequence. However, in the latter case amino acid changes are preferably of a minor nature, i.e. conservative amino acid substitutions that do not significantly affect the folding or activity of the protein, small deletions, typically of from one to about 30 amino acids; small amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain. See in general Ford et al., Protein Expression and Purification 2: 95-107, 1991. Examples of conservative substitutions are substitutions within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine).

It will be apparent to persons skilled in the art that such substitutions can be made outside the regions critical to the function of the molecule and still result in an active polypeptide. Amino acids essential to the activity of the polypeptide encoded by the DNA construct of the invention, and therefore preferably not subject to substitution, may be identified according to procedures known in the art, such as site-directed mutagenesis or alanine-scanning mutagenesis (Cunningham and Wells, *Science* 244, 1081–1085, 1989). In the latter technique mutations are introduced at every residue in the molecule, and the resultant mutant molecules are tested for biological (i.e. lipolytic) activity to identify amino acid residues that are critical to the activity of the molecule. Sites of substrate-enzyme interaction can also be determined by analysis of crystal structure as determined by such techniques as nuclear magnetic resonance, crystallography or photoaffinity labeling. See, for example, de Vos et al., *Science* 255: 306–312, 1992; Smith et al., *J. Mol. Biol.* 224: 899–904, 1992; Wlodaver e t al., *FEBS Lett.* 309: 59–64, 1992.

The homology referred to in i) above is determined as the degree of identity between the two sequences indicating a derivation of the first sequence from the second. The homology may suitably be determined by means of computer programs known in the art such as GAP provided in the GCG program package (Needleman, S. B. and Wunsch, C. D., *Journal of Molecular Biology*, 48: 443–453, 1970). Using GAP with the following settings for DNA sequence comparison: GAP creation penalty of 5.0 and GAP extension penalty of 0.3, the coding region of the DNA sequence exhibits a degree of identity preferably of at least 40%, more preferably at least 50%, more preferably at least 60%, more preferably at least 70%, even more preferably at least 80%, especially at least 90%, with the coding region of the DNA sequence shown in SEQ ID No.1 or the DNA sequence encoding a lipolytic enzyme, which is obtainable from the plasmid in *Saccharomyces cerevisiae* DSM 9975.

The hybridization referred to in ii) above is intended to indicate that the analogous DNA sequence hybridizes to the same probe as the DNA sequence encoding the lipolytic enzyme under certain specified conditions which are described in detail in the Materials and Methods section hereinafter. Normally, the analogous DNA sequence is highly homologous to the DNA sequence, such as at least 70% homologous to the sequence shown in SEQ ID No.1 encoding a lipolytic enzyme of the invention, such as at least 75%, at least 80%, at least 85%, at least 90% or even at least 95% homologous to the DNA sequence shown in SEQ ID No. 1.

The degree of homology referred to in iii) above is determined as the degree of identity between the two sequences indicating a derivation of the first sequence from the second. The homology may suitably be determined by means of computer programs known in the art such as GAP provided in the GCG program package (Needleman, S. B. and Wunsch, C. D., *Journal of Molecular Biology*, 48: 443–453, 1970). Using GAP with the following settings for polypeptide sequence comparison: GAP creation penalty of 3.0 and GAP extension penalty of 0.1, the polypeptide encoded by an analogous DNA sequence exhibits a degree of identity preferably of at least 70%, more preferably at least 80%, especially at least 90%, with the enzyme encoded by a DNA construct comprising the DNA sequence shown in SEQ ID No.1 or the DNA sequence encoding a lipolytic enzyme, which is obtainable from the plasmid in *Saccharomyces cerevisiae* DSM 9975, the amino acid sequence of which enzyme is shown in SEQ ID No. 2.

The term "derived from" in connection with property iv) above is intended not only to indicate a lipolytic enzyme produced by *H. insolens* strain DSM 1800, but also a lipolytic enzyme encoded by a DNA sequence isolated from strain DSM 1800 and produced in a host organism transformed with said DNA sequence. The immunological reactivity may be determined by the method described in the Materials and Methods section below.

In further aspects, the invention relates to an expression vector harboring a DNA construct of the invention, a cell comprising the DNA construct or expression vector, and a method of producing an enzyme exhibiting lipolytic activity, which method comprises culturing said cell under conditions permitting the production of the enzyme, and recovering the enzyme from the culture.

In a still further aspect the invention relates to an enzyme exhibiting lipolytic activity, which enzyme a) is encoded by a DNA construct of the invention, and/or b) is produced by the method of the invention, and/or c) is immunologically reactive with an antibody raised against a purified lipolytic enzyme which is encoded by the DNA sequence shown in SEQ ID No. 1 and/or by the DNA sequence encoding a lipolytic enzyme, which is obtainable from the plasmid in *Saccharomyces cerevisiae* DSM 9975, and/or which is derived from *Humicola insolens* DSM 1800.

In a still further aspect, the present invention relates to a detergent additive or a detergent composition comprising an enzyme of the invention.

DETAILED DESCRIPTION OF THE INVENTION

Figure 1:
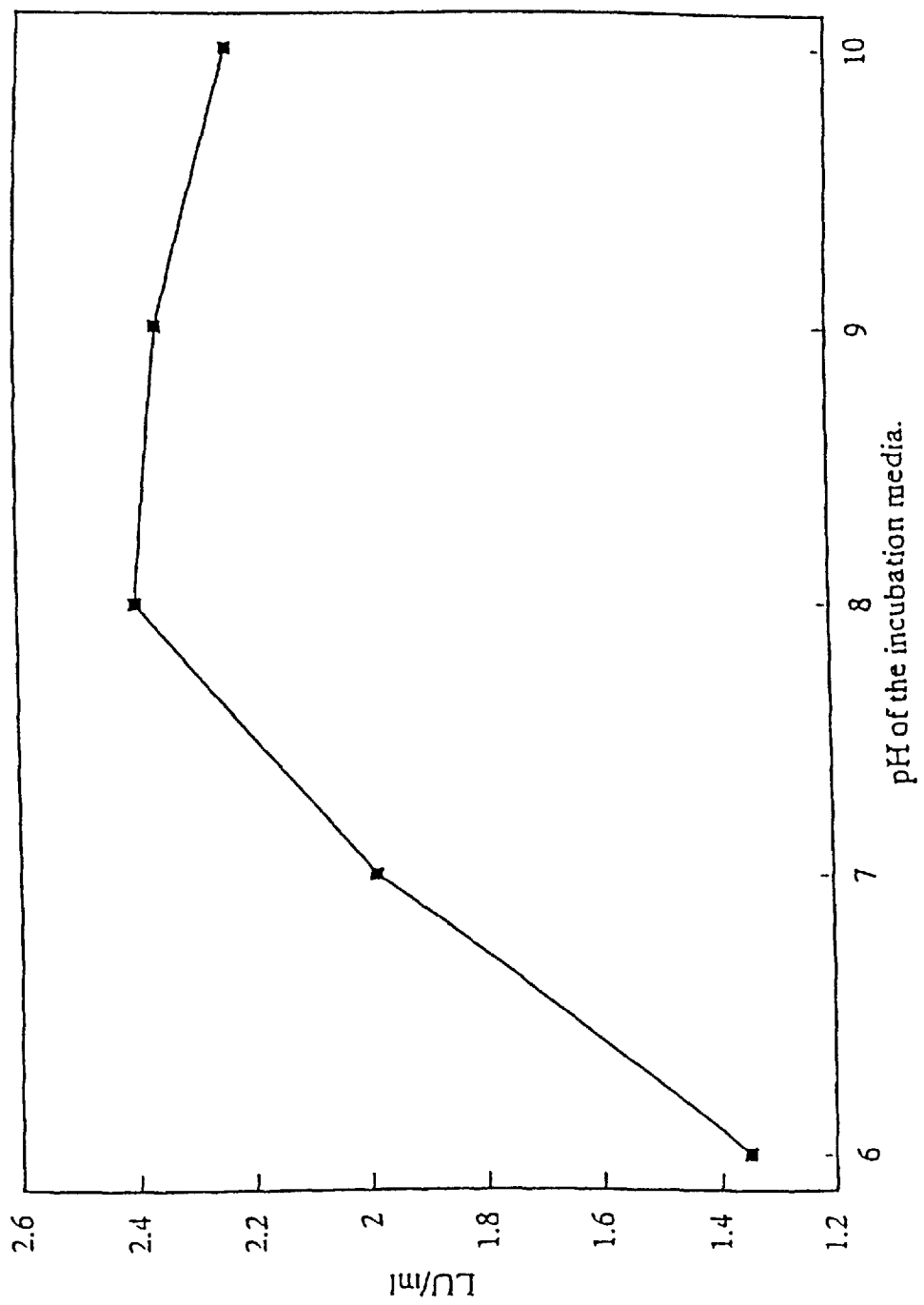

The DNA sequence of the invention encoding an enzyme exhibiting lipolytic activity may be isolated by a general method involving cloning, in suitable vectors, a DNA library from *H. insolens*, transforming suitable yeast host cells with said vectors, culturing the host cells under suitable conditions to express any enzyme of interest encoded by a clone in the DNA library, screening for positive clones by determining any lipolytic activity of the enzyme produced by such clones, and isolating the enzyme-encoding DNA from such clones.

The general method is further disclosed in WO 94/14953. A more detailed description of the screening method is given in Example 1 below.

The DNA sequence coding for the enzyme may, for instance, be isolated by screening a cDNA library of *H. insolens*, e.g. strain DSM 1800 publicly available from DSM (Deutsche Sammlung von Mikroorganismen und Zellkulturen, Mascheroder Weg 1 b, D-38124 Braunschweig, Germany) and selecting for clones expressing the appropriate enzyme activity (i.e. lipolytic activity), or isolated from *Saccharomyces cerevisiae* DSM 9975 deposited under the Budapest Treaty on May 11, 1995, at DSM. The appropriate DNA sequence may then be isolated from the clone by standard procedures, e.g. as described in Example 1.

It is expected that a DNA sequence coding for a homologous enzyme, i.e. an analogous DNA sequence, is obtainable from other microorganisms. For instance, the DNA sequence may be derived by similarly screening a cDNA library of another microorganism, in particular a fungus, especially a fungus from the order Sordariales, such as a strain of a Thielavia sp., in particular *T. terrestris*, a strain of a Chaetomium sp., in particular *C. elatum* or *C. globosum*, a strain of a Gelasinospora sp., in particular *G. cerealis*, a strain of a Neurospora sp., in particular *N. crassa*, a strain of a Podospora sp., in particular *P. anserina*, a strain of a Sordaria sp., in particular *S. fimicola* or *S. macrospora*, or a strain of another Humicola sp.. Other fungi of interest include strains of Aspergillus sp., such as *A. aculeatus* or *A. niger*, strains of Trichoderma sp., such as *T. harzianum, T reeseii, T. viride, T. longibrachiatum* or *T. koningli*, or strains of Fusarium sp., such as *F. oxysporum*.

Alternatively, the DNA coding for a lipolytic enzyme of the invention may, in accordance with well-known procedures, conveniently be isolated from DNA from a suitable source, such as any of the above mentioned organisms, by use of synthetic oligonucleotide probes prepared on the basis of a DNA sequence disclosed herein. For instance, a suitable oligonucleotide probe may be prepared on the basis of the DNA sequence shown in SEQ ID No. 1 or the amino acid sequence shown in SEQ ID No. 2, or any suitable subsequence of any of these sequences.

The DNA sequence may subsequently be inserted into a recombinant expression vector. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the lipolytic enzyme should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the lipolytic enzyme the promoter and the terminator, respectively, and to insert them into suitable vectors are well known to persons skilled in the art (cf., for instance, Sambrook et al., *Molecular Cloning. A Laboratory Manual*, Cold Spring Harbor, N.Y., 1989).

The host cell which is transformed with the DNA sequence encoding the enzyme of the invention is preferably a eucaryotic cell, in particular a fungal cell such as a yeast or filamentous fungal cell. In particular, the cell may belong to a species of Aspergillus, most preferably *A. oryzae* or *A. niger*. Alternatively, the cell may belong to a species of Trichoderma, such as *T. reeseii*, or a species of Fusarium, such as *F. oxysporum* or *F. graminearum*. Fungal cells may be transformed by a process involving protoplast formation and transformation of the protoplasts followed by regeneration of the cell wall in a manner known per se. The use of *Aspergillus* as a host microorganism is described in EP 0 238 023 (Novo Nordisk A/S). The host cell may also be a yeast cell, e.g. a strain of Saccharomyces, in particular *Saccharomyces cerevisiae, Saccharomyces kluyveri* or *Saccharomyces uvarum*, a strain of Schizosaccharomyces sp., such as *Schizosaccharomyces pombe*, or a strain of Hansenula sp., Pichia sp., Yarrowia sp., such as *Yarrowia lipolytica*, or Kluyveromyces sp., such as *Kluyveromyces lactis*.

In a still further aspect, the present invention relates to a method of producing an enzyme according to the invention, wherein a suitable host cell transformed with a DNA sequence encoding the enzyme is cultured under conditions permitting the production of the enzyme, and the resulting enzyme is recovered from the culture.

The medium used to culture the transformed host cells may be any conventional medium suitable for growing the host cells in question. The expressed lipolytic enzyme may conveniently be secreted into the culture medium and may be recovered herefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

THE ENZYME OF THE INVENTION

The enzyme of the invention is one which is encoded by the DNA construct of the invention.

A preferred enzyme of the invention may also be characterized by having one or more of the following characteristics:

it has a molecular weight of about 20–21 kDa it has a pI in the range of 7–9, such as about 8 it has a pH optimum in the range of about 6–10, such as in the range of 7–9, e.g. about 8 it has specificity, or at least exhibits greatest lipolytic activity, towards short-chain lipid substrates.

The enzyme of the invention is preferably obtainable from a strain of Humicola, such as a strain of *H. insolens* or from a strain of any of the various organisms mentioned as suitable sources of a DNA sequence encoding a homologous enzyme.

DETERGENT COMPOSITION

According to the invention, the lipolytic enzyme of the invention may typically be a component of a detergent composition (e.g. a detergent composition for laundry or textile washing). As such, it may be included in the detergent composition in the form of a non-dusting granulate, a stabilized liquid, or a protected enzyme. Non-dusting granulates may be produced, e.g., as disclosed in U.S. Pat. No. 4,106,991 and 4,661,452 (both to Novo Industri A/S) and may optionally be coated by methods known in the art. Examples of waxy coating materials are polytethylene oxide) products (polyethyleneglycol, PEG) with mean molar weights of 1000 to 20000, ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238, 216.

The detergent composition of the invention may be in any convenient form, e.g. as powder, granules, paste or liquid. A liquid detergent may be aqueous, typically containing up to 70% water and 0–30% organic solvent, or nonaqueous.

The detergent composition comprises one or more surfactants, each of which may be anionic, nonionic, cationic, or zwitterionic. The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0–40% of nonionic surfactant such as alcohol ethoxylate (AEO or AE), carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as another lipolytic enzyme (lipase), an amylase, a cutinase, a protease, a cellulase, a peroxidase, or an oxidase, e.g. a laccase.

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2 O_2$ source such as perborate or percarbonate which may be combined with a peracid-forming bleach activator such as tetraacetylethylenediamine (TAED) or nonanoyloxybenzenesulfonate (NOBS). Alternatively, the bleaching system may comprise peroxyacids of, e.g., the amide, imide, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil-redeposition agents, dyes, bactericides, optical brighteners, or perfume.

The pH (measured in aqueous solution at use concentration) will usually be neutral or alkaline, e.g. in the range of 7–11.

Particular forms of detergent compositions within the scope of the invention include:

1) A detergent composition formulated as a granulate having a bulk density of at least 600 g/l comprising

| | |
|---|---|
| Linear alkylbenzenesulfonate (calculated as acid) | 7–12% |
| Alcohol ethoxysulfate (e.g. $C_{12-18}$ alcohol, 1–2 EO) or alkyl sulfate (e.g. $C_{16-18}$) | 1–4% |
| Alcohol ethoxylate (e.g. $C_{14-15}$ alcohol, 7 EO) | 5–9% |
| Sodium carbonate (as $Na_2CO_3$) | 14–20% |
| Soluble silicate (as $Na_2O,2SiO_2$) | 2–6% |
| Zeolite (as $NaAlSiO_4$) | 15–22% |
| Sodium sulfate (as $Na_2SO_4$) | 0–6% |
| Sodium citrate/citric acid (as $C_6H_5Na_3O_7/C_6H_8O_7$) | 0–15% |
| Sodium perborate (as $NaBO_3.H_2O$) | 11–18% |
| TAED | 2–6% |
| Carboxymethylcellulose | 0–2% |
| Polymers (e.g. maleic/acrylic acid copolymer, PVP, PEG) | 0–3% |
| Enzymes (calculated as pure enzyme protein) | 0.0001–0.1% |
| Minor ingredients (e.g. suds suppressors, perfume, optical brightener, photobleach) | 0–5% |

2) A detergent composition formulated as a granulate having a bulk density of at least 600 g/l comprising

| | |
|---|---|
| Linear alkylbenzenesulfonate (calculated as acid) | 6–11% |
| Alcohol ethoxysulfate (e.g. $C_{12-18}$ alcohol, 1–2 EO or alkyl sulfate (e.g. $C_{16-18}$) | 1–3% |
| Alcohol ethoxylate (e.g. $C_{14-15}$ alcohol, 7 EO) | 5–9% |
| Sodium carbonate (as $Na_2CO_3$) | 15–21% |
| Soluble silicate (as $Na_2O,2SiO_2$) | 1–4% |
| Zeolite (as $NaAlSiO_4$) | 24–34% |
| Sodium sulfate (as $Na_2SO_4$) | 4–10% |
| Sodium citrate/citric acid (as $C_6H_5Na_3O_7/C_6H_8O_7$) | 0–15% |
| Carboxymethylcellulose | 0–2% |
| Polymers (e.g. maleic/acrylic acid copolymer, PVP, PEG) | 1–6% |
| Enzymes (calculated as pure enzyme protein) | 0.0001–0.1% |
| Minor ingredients (e.g. suds suppressors, perfume) | 0–5% |

3) A detergent composition formulated as a granulate having a bulk density of at least 600 g/l comprising

| | |
|---|---|
| Linear alkylbenzenesulfonate (calculated as acid) | 5–9% |
| Alcohol ethoxylate (e.g. $C_{12-15}$ alcohol, 7 EO) | 7–14% |
| Soap as fatty acid (e.g. $C_{16-22}$ fatty acid) | 1–3% |
| Sodium carbonate (as $Na_2CO_3$) | 10–17% |
| Soluble silicate (as $Na_2O,2SiO_2$) | 3–9% |
| Zeolite (as $NaAlSiO_4$) | 23–33% |
| Sodium sulfate (as $Na_2SO_4$) | 0–4% |
| Sodium perborate (as $NaBO_3.H_2O$) | 8–16% |
| TAED | 2–8% |
| Phosphonate (e.g. EDTMPA) | 0–1% |
| Carboxymethylcellulose | 0–2% |
| Polymers (e.g. maleic/acrylic acid copolymer, PVP, PEG) | 0–3% |
| Enzymes (calculated as pure enzyme protein) | 0.0001–0.1% |
| Minor ingredients (e.g. suds suppressors, perfume, optical brightener) | 0–5% |

4) A detergent composition formulated as a granulate having a bulk density of at least 600 g/l comprising

| | |
|---|---|
| Linear alkylbenzenesulfonate (calculated as acid) | 8–12% |
| Alcohol ethoxylate (e.g. $C_{12-15}$ alcohol, 7 EO) | 10–25% |
| Sodium carbonate (as $Na_2CO_3$) | 14–22% |
| Soluble silicate (as $Na_2O,2SiO_2$) | 1–5% |
| Zeolite (as $NaAlSiO_4$) | 25–35% |
| Sodium sulfate (as $Na_2SO_4$) | 0–10% |

-continued

| | |
|---|---|
| Carboxymethylcellulose | 0–2% |
| Polymers (e.g. maleic/acrylic acid copolymer, PVP, PEG) | 1–3% |
| Enzymes (calculated as pure enzyme protein) | 0.0001–0.1% |
| Minor ingredients (e.g. suds suppressors, perfume) | 0–5% |

5) An aqueous liquid detergent composition comprising

| | |
|---|---|
| Linear alkylbenzenesulfonate (calculated as acid) | 15–21% |
| Alcohol ethoxylate (e.g. $C_{12-15}$ alcohol, 7 EO or $C_{12-15}$ alcohol, 5 EO) | 12–18% |
| Soap as fatty acid (e.g. oleic acid) | 3–13% |
| Alkenylsuccinic acid ($C_{12-14}$) | 0–13% |
| Aminoethanol | 8–18% |
| Citric acid | 2–8% |
| Phosphonate | 0–3% |
| Polymers (e.g. PVP, PEG) | 0–3% |
| Borate (as $B_4O_7$) | 0–2% |
| Ethanol | 0–3% |
| Propylene glycol | 8–14% |
| Enzymes (calculated as pure enzyme protein) | 0.0001–0.1% |
| Minor ingredients (e.g. dispersants, suds suppressors, perfume, optical brightener) | 0–5% |

6) An aqueous structured liquid detergent composition comprising

| | |
|---|---|
| Linear alkylbenzenesulfonate (calculated as acid) | 15–21% |
| Alcohol ethoxylate (e.g. $C_{12-15}$ alcohol, 7 EO, or $C_{12-15}$ alcohol, 5 EO) | 3–9% |
| Soap as fatty acid (e.g. oleic acid) | 3–10% |
| Zeolite (as $NaAlSiO_4$) | 14–22% |
| Potassium citrate | 9–18% |
| Borate (as $B_4O_7$) | 0–2% |
| Carboxymethylcellulose | 0–2% |
| Polymers (e.g. PEG, PVP) | 0–3% |
| Anchoring polymers such as, e.g., lauryl methacrylate/acrylic acid copolymer; molar ratio 25:1; MW3800 | 0–3% |
| Glycerol | 0–5% |
| Enzymes (calculated as pure enzyme protein) | 0.0001–0.1% |
| Minor ingredients (e.g. dispersants, suds suppressors, perfume, optical brighteners) | 0–5% |

7) A detergent composition formulated as a granulate having a bulk density of at least 600 g/l comprising

| | |
|---|---|
| Fatty alcohol sulfate | 5–10% |
| Ethoxylated fatty acid monoethanolamide | 3–9% |
| Soap as fatty acid | 0–3% |
| Sodium carbonate (as $Na_2CO_3$) | 5–10% |
| Soluble silicate (as $Na_2O,2SiO_2$) | 1–4% |
| Zeolite (as $NaAlSiO_4$) | 20–40% |
| Sodium sulfate (as $Na_2SO_4$) | 2–8% |
| Sodium perborate (as $NaBO_3.H_2O$) | 12–18% |
| TAED | 2–7% |
| Polymers (e.g. maleic/acrylic acid copolymer, PEG) | 1–5% |
| Enzymes (calculated as pure enzyme protein) | 0.0001–0.1% |
| Minor ingredients (e.g. optical brightener, suds suppressors, perfume) | 0–5% |

8) A detergent composition formulated as a granulate comprising

| | |
|---|---|
| Linear alkylbenzenesulfonate (calculated as acid) | 8–14% |
| Ethoxylated fatty acid monoethanolamide | 5–11% |
| Soap as fatty acid | 0–3% |
| Sodium carbonate (as $Na_2CO_3$) | 4–10% |
| Soluble silicate (as $Na_2O,2SiO_2$) | 1–4% |
| Zeolite (as $NaAlSiO_4$) | 30–50% |
| Sodium sulfate (as $Na_2SO_4$) | 3–11% |
| Sodium citrate (as $C_6H_5Na_3O_7$) | 5–12% |
| Polymers (e.g. PVP, maleic/acrylic acid copolymer, PEG) | 1–5% |
| Enzymes (calculated as pure enzyme protein) | 0.0001–0.1% |
| Minor ingredients (e.g. suds suppressors, perfume) | 0–5% |

9) A detergent composition formulated as a granulate comprising

| | |
|---|---|
| Linear alkylbenzenesulfonate (calculated as acid) | 6–12% |
| Nonionic surfactant | 1–4% |
| Soap as fatty acid | 2–6% |
| Sodium carbonate (as $Na_2CO_3$) | 14–22% |
| Zeolite (as $NaAlSiO_4$) | 18–32% |
| Sodium sulfate (as $Na_2SO_4$) | 5–20% |
| Sodium citrate (as $C_6H_5Na_3O_7$) | 3–8% |
| Sodium perborate (as $NaBO_3.H_2O$) | 4–9% |
| Bleach activator (e.g. NOBS or TAED) | 1–5% |
| Carboxymethylcellulose | 0–2% |
| Polymers (e.g. polycarboxylate or PEG) | 1–5% |
| Enzymes (calculated as pure enzyme protein) | 0.0001–0.1% |
| Minor ingredients (e.g. optical brightener, perfume) | 0–5% |

10) An aqueous liquid detergent composition comprising

| | |
|---|---|
| Linear alkylbenzenesulfonate (calculated as acid) | 15–23% |
| Alcohol ethoxysulfate (e.g. $C_{12-15}$ alcohol, 2–3 EO) | 8–15% |
| Alcohol ethoxylate (e.g. $C_{12-15}$ alcohol, 7 EO, or $C_{12-15}$ alcohol, 5 EO) | 3–9% |
| Soap as fatty acid (e.g. lauric acid) | 0–3% |
| Aminoethanol | 1–5% |
| Sodium citrate | 5–10% |
| Hydrotrope (e.g. sodium toluensulfonate) | 2–6% |
| Borate (as $B_4O_7$) | 0–2% |
| Carboxymethylcellulose | 0–1% |
| Ethanol | 1–3% |
| Propylene glycol | 2–5% |
| Enzymes (calculated as pure enzyme protein) | 0.0001–0.1% |
| Minor ingredients (e.g. polymers, dispersants, perfume, optical brighteners) | 0–5% |

11) An aqueous liquid detergent composition comprising

| | |
|---|---|
| Linear alkylbenzenesulfonate (calculated as acid) | 20–32% |
| Alcohol ethoxylate (e.g. $C_{12-15}$ alcohol, 7 EO, or $C_{12-15}$ alcohol, 5 EO) | 6–12% |
| Aminoethanol | 2–6% |
| Citric acid | 8–14% |
| Borate (as $B_4O_7$) | 1–3% |
| Polymer (e.g. maleic/acrylic acid copolymer, anchoring polymer such as, e.g., lauryl methacrylate/acrylic acid copolymer) | 0–3% |

-continued

| | |
|---|---|
| Glycerol | 3–8% |
| Enzymes (calculated as pure enzyme protein) | 0.0001–0.1% |
| Minor ingredients (e.g. hydrotropes, dispersants, perfume, optical brighteners) | 0–5% |

12) A detergent composition formulated as a granulate having a bulk density of at least 600 g/l comprising

| | |
|---|---|
| Anionic surfactant (linear alkylbenzene-sulfonate, alkyl sulfate, alpha-olefinsulfonate, alpha-sulfo fatty acid methyl esters, alkanesulfonates, soap) | 25–40% |
| Nonionic surfactant (e.g. alcohol ethoxylate) | 1–10% |
| Sodium carbonate (as $Na_2CO_3$) | 8–25% |
| Soluble silicates (as $Na_2O, 2SiO_2$) | 5–15% |
| Sodium sulfate (as $Na_2SO_4$) | 0–5% |
| Zeolite (as $NaAlSiO_4$) | 15–28% |
| Sodium perborate (as $NaBO_3.4H_2O$) | 0–20% |
| Bleach activator (TAED or NOBS) | 0–5% |
| Enzymes (calculated as pure enzyme protein) | 0.0001–0.1% |
| Minor ingredients (e.g. perfume, optical brighteners) | 0–3% |

13) Detergent formulations as described in 1)–12) wherein all or part of the linear alkylbenzenesulfonate is replaced by ($C_{12}$–$C_{18}$) alkyl sulfate.

14) A detergent composition formulated as a granulate having a bulk density of at least 600 g/l comprising

| | |
|---|---|
| ($C_{12}$–$C_{18}$) alkyl sulfate | 9–15% |
| Alcohol ethoxylate | 3–6% |
| Polyhydroxy alkyl fatty acid amide | 1–5% |
| Zeolite (as $NaAlSiO_4$) | 10–20% |
| Layered disilicate (e.g. SK56 from Hoechst) | 10–20% |
| Sodium carbonate (as $Na_2CO_3$) | 3–12% |
| Soluble silicate (as $Na_2O,2SiO_2$) | 0–6% |
| Sodium citrate | 4–8% |
| Sodium percarbonate | 13–22% |
| TAED | 3–8% |
| Polymers (e.g. polycarboxylates and PVP=) | 0–5% |
| Enzymes (calculated as pure enzyme protein) | 0.0001–0.1% |
| Minor ingredients (e.g. optical brightener, photo bleach, perfume, suds suppressors) | 0–5% |

15) A detergent composition formulated as a granulate having a bulk density of at least 600 g/l comprising

| | |
|---|---|
| ($C_{12}$–$C_{18}$) alkyl sulfate | 4–8% |
| Alcohol ethoxylate | 11–15% |
| Soap | 1–4% |
| Zeolite MAP or zeolite A | 35–45% |
| Sodium carbonate (as $Na_2CO_3$) | 2–8% |
| Soluble silicate (as $Na_2O,2SiO_2$) | 0–4% |
| Sodium percarbonate | 13–22% |
| TAED | 1–8% |
| Carboxymethyl cellulose | 0–3% |
| Polymers (e.g. polycarboxylates and PVP) | 0–3% |
| Enzymes (calculated as pure enzyme protein) | 0.0001–0.1% |
| Minor ingredients (e.g. optical brightener, phosphonate, perfume) | 0–3% |

16) Detergent formulations as described in 1)–15) which contain a stabilized or encapsulated peracid, either as an additional component or as a substitute for already specified bleach systems.

17) Detergent compositions as described in 1), 3), 7), 9) and 12) wherein perborate is replaced by percarbonate.

18) Detergent compositions as described in 1), 3), 7), 9), 12), 14) and 15) which additionally contain a manganese catalyst. The manganese catalyst may, e.g., be one of the compounds described in "Efficient manganese catalysts for low-temperature bleaching", Nature 369, 1994, pp. 637–639.

19) A detergent composition formulated as a nonaqueous detergent liquid comprising a liquid nonionic surfactant such as, e.g., linear alkoxylated primary alcohol, a builder system (e.g. phosphate), enzyme and alkali. The detergent may also comprise anionic surfactant and/or a bleach system.

Dishwashing Composition

A lipolytic enzyme of the invention may suitably be a component of a dishwashing detergent composition. The dishwashing detergent composition will comprise a surfactant which may be anionic, non-ionic, cationic, amphoteric or a mixture of these types. The detergent will contain 0–90% of non-ionic surfactant, such as low- to non-foaming ethoxylated propoxylated straight-chain alcohols.

The detergent composition may contain detergent builder salts of inorganic and/or organic types. The detergent builders may be subdivided into phosphorus-containing and non-phosphorus-containing types. The detergent composition usually contains 1–90% of detergent builders.

Examples of phosphorus-containing inorganic alkaline detergent builders, when present, include water-soluble salts, especially alkali metal pyrophosphates, orthophosphates, polyphosphates, and phosphonates. Examples of non-phosphorus-containing inorganic builders, when present, include water-soluble alkali metal carbonates, borates and silicates as well as the various types of water-insoluble crystalline or amorphous alumino silicates of which zeolites are the best-known representatives.

Examples of suitable organic builders include the alkali metal, ammonium and substituted ammonium, citrates, succinates, malonates, fatty acid sulphonates, carboxymethoxy succinates, ammonium polyacetates, carboxylates, polycarboxylates, aminopolycarboxylates, polyacetal carboxylates and polyhydroxsulphonates.

Other suitable organic builders include the higher molecular weight polymers and co-polymers known to have builder properties, for example appropriate polyacrylic acid, polymaleic and polyacrylic/polymaleic acid copolymers and their salts.

The dishwashing detergent composition may contain bleaching agents of the chlorine/bromine-type or the oxygen-type. Examples of inorganic chlorine/bromine-type bleaches are lithium, sodium or calcium hypochlorite and hypobromite, as well as chlorinated trisodium phosphate. Examples of organic chlorine/bromine-type bleaches are heterocyclic N-bromo and N-chloro imides such as trichloroisocyanuric, tribromoisocyanuric, dibromoisocyanuric and dichloroisocyanuric acids, and salts thereof with water-solubilizing cations such as potassium and sodium. Hydantoin compounds are also suitable.

The oxygen bleaches are preferred, for example in the form of an inorganic persalt, preferably with a bleach precursor or as a peroxy acid compound. Typical examples of suitable peroxy bleach compounds are alkali metal perborates, both tetrahydrates and monohydrates, alkali metal percarbonates, persilicates and perphosphates. Preferred activator materials are TAED and glycerol triacetate.

The dishwashing detergent composition of the invention may be stabilized using conventional stabilizing agents for the enzyme(s), e.g. a polyol such as e.g. propylene glycol, a sugar or a sugar alcohol, lactic acid, boric acid, or a boric acid derivative, e.g. an aromatic borate ester.

The dishwashing detergent composition may also comprise other enzymes, in particular an amylase, a protease and/or a cellulase.

The dishwashing detergent composition of the invention may also contain other conventional detergent ingredients, e.g. deflocculant material, filler material, foam depressors, anti-corrosion agents, soil-suspending agents, sequestering agents, anti-soil redeposition agents, dehydrating agents, dyes, bactericides, fluorescers, thickeners and perfumes.

Below, specifically preferred dishwashing compositions are exemplified:

1) POWDER AUTOMATIC DISHWASHING COMPOSITION

| | |
|---|---|
| Nonionic surfactant | 0.4–2.5% |
| Sodium metasilicate | 0–20% |
| Sodium disilicate | 3–20% |
| Sodium triphosphate | 20–40% |
| Sodium carbonate | 0–20% |
| Sodium perborate | 2–9% |
| Tetraacetyl ethylene diamine (TAED) | 1–4% |
| Sodium sulphate | 5–33% |
| Enzymes | 0.0001–0.1% |

2) POWDER AUTOMATIC DISHWASHING COMPOSITION

| | |
|---|---|
| Nonionic surfactant (e.g. alcohol ethoxylate) | 1–2% |
| Sodium disilicate | 2–30% |
| Sodium carbonate | 10–50% |
| Sodium phosphonate | 0–5% |
| Trisodium citrate dihydrate | 9–30% |
| Nitrilotrisodium acetate (NTA) | 0–20% |
| Sodium perborate monohydrate | 5–10% |
| Tetraacetyl ethylene diamine (TAED) | 1–2% |
| Polyacrylate polymer (e.g. maleic acid/acrylic acid copolymer) | 6–25% |
| Enzymes | 0.0001–0.1% |
| Perfume | 0.1–0.5% |
| Water | 5–10 |

3) POWDER AUTOMATIC DISHWASHING COMPOSITION

| | |
|---|---|
| Nonionic surfactant | 0.5–2.0% |
| Sodium disilicate | 25–40% |
| Sodium citrate | 30–55% |
| Sodium carbonate | 0–29% |
| Sodium bicarbonate | 0–20% |
| Sodium perborate monohydrate | 0–15% |
| Tetraacetyl ethylene diamine (TAED) | 0–6% |
| Maleic acid/acrylic acid copolymer | 0–5% |
| Clay | 1–3% |
| Polyamino acids | 0–20% |
| Sodium polyacrylate | 0–8% |
| Enzymes | 0.0001–0.1% |

4) POWDER AUTOMATIC DISHWASHING COMPOSITION

| | |
|---|---|
| Nonionic surfactant | 1–2% |
| Zeolite MAP | 15–42% |
| Sodium disilicate | 30–34% |
| Sodium citrate | 0–12% |
| Sodium carbonate | 0–20% |
| Sodium perborate monohydrate | 7–15% |
| Tetraacetyl ethylene diamine (TAED) | 0–3% |
| Polymer | 0–4% |
| Maleic acid/acrylic acid copolymer | 0–5% |
| Organic phosphonate | 0–4% |
| Clay | 1–2% |
| Enzymes | 0.0001–0.1% |
| Sodium sulphate | Balance |

5) POWDER AUTOMATIC DISHWASHING COMPOSITION

| | |
|---|---|
| Nonionic surfactant | 1–7% |
| Sodium disilicate | 18–30% |
| Trisodium citrate | 10–24% |
| Sodium carbonate | 12–20% |
| Monopersulphate (2 $KHSO_5 \cdot KHSO_4 \cdot K_2SO_4$) | 15–21% |
| Bleach stabilizer | 0.1–2% |
| Maleic acid/acrylic acid copolymer | 0–6% |
| Diethylene triamine pentaacetate, pentasodium salt | 0–2.5% |
| Enzymes | 0.0001–0.1% |
| Sodium sulphate, water | Balance |

6) POWDER AND LIQUID DISHWASHING COMPOSITION WITH CLEANING SURFACTANT SYSTEM

| | |
|---|---|
| Nonionic surfactant | 0–1.5% |
| Octadecyl dimethylamine N-oxide dihydrate | 0–5% |
| 80:20 wt. C18/C16 blend of octadecyl dimethylamine N-oxide dihydrate and hexadecyldimethyl amine N-oxide dihydrate | 0–4% |
| 70:30 wt. C18/C16 blend of octadecyl bis (hydroxyethyl)amine N-oxide anhydrous and hexadecyl bis (hydroxyethyl)amine N-oxide anhydrous | 0–5% |
| $C_{13}$–$C_{15}$ alkyl ethoxysulfate with an average degree of ethoxylation of 3 | 0–10% |
| $C_{12}$–$C_{15}$ alkyl ethoxysulfate with an average degree of ethoxylation of 3 | 0–5% |
| $C_{13}$–$C_{15}$ ethoxylated alcohol with an average degree of ethoxylation of 12 | 0–5% |
| A blend of $C_{12}$–$C_{15}$ ethoxylated alcohols with an average degree of ethoxylation of 9 | 0–6.5% |
| A blend of $C_{12}$–$C_{15}$ ethoxylated alcohols with an average degree of ethoxylation of 30 | 0–4% |
| Sodium disilicate | 0–33% |
| Sodium tripolyphosphate | 0–46% |
| Sodium citrate | 0–28% |
| Citric acid | 0–29% |
| Sodium carbonate | 0–20% |
| Sodium perborate monohydrate | 0–11.5% |
| Tetraacetyl ethylene diamine (TAED) | 0–4% |
| Maleic acid/acrylic acid copolymer | 0–7.5% |
| Sodium sulphate | 0–12.5% |
| Enzymes | 0.0001–0.1% |

7) NON-AQUEOUS LIQUID AUTOMATIC DISHWASHING COMPOSITION

| | |
|---|---|
| Liquid nonionic surfactant (e.g. alcohol ethoxylates) | 2.0–10.0% |
| Alkali metal silicate | 3.0–15.0% |
| Alkali metal phosphate | 20.0–40.0% |
| Liquid carrier selected from higher glycols, polyglycols, polyoxides, glycolethers | 25.0–45.0% |
| Stabilizer (e.g. a partial ester of phosphoric acid and a $C_{16}$–$C_{18}$ alkanol) | 0.5–7.0% |
| Foam suppressor (e.g. silicone) | 0–1.5% |
| Enzymes | 0.0001–0.1% |

8) NON-AQUEOUS LIQUID DISHWASHING COMPOSITION

| | |
|---|---|
| Liquid nonionic surfactant (e.g. alcohol ethoxylates) | 2.0–10.0% |
| Sodium silicate | 3.0–15.0% |
| Alkali metal carbonate | 7.0–20.0% |
| Sodium citrate | 0.0–1.5% |
| Stabilizing system (e.g. mixtures of finely divided silicone and low molecular weight dialkyl polyglycol ethers) | 0.5–7.0% |
| Low molecule weight polyacrylate polymer | 5.0%–15.0% |
| Clay gel thickener (e.g. bentonite) | 0.0–10.0% |
| Hydroxypropyl cellulose polymer | 0.0–0.6% |
| Enzymes | 0.0001–0.1% |
| Liquid carrier selected from higher lycols, polyglycols, polyoxides and glycol ethers | Balance |

9) THIXOTROPIC LIQUID AUTOMATIC DISHWASHING COMPOSITION

| | |
|---|---|
| $C_{12}$–$C_{14}$ fatty acid | 0–0.5% |
| Block co-polymer surfactant | 1.5–15.0% |
| Sodium citrate | 0–12% |
| Sodium tripolyphosphate | 0–15% |
| Sodium carbonate | 0–8% |
| Aluminium tristearate | 0–0.1% |
| Sodium cumene sulphonate | 0–1.7% |
| Polyacrylate thickener | 1.32–2.5% |
| Sodium polyacrylate | 2.4–6.0% |
| Boric acid | 0–4.0% |
| Sodium formate | 0–0.45% |
| Calcium formate | 0–0.2% |
| Sodium n-decydiphenyl oxide disulphonate | 0–4.0% |
| Monoethanol amine (MEA) | 0–1.86% |
| Sodium hydroxide (50%) | 1.9–9.3% |
| 1,2-Propanediol | 0–9.4% |
| Enzymes | 0.0001–0.1% |
| Suds suppressor, dye, perfumes, water | Balance |

10) LIQUID AUTOMATIC DISHWASHING COMPOSITION

| | |
|---|---|
| Alcohol ethoxylate | 0–20% |
| Fatty acid ester sulphonate | 0–30% |
| Sodium dodecyl sulphate | 0–20% |
| Alkyl polyglycoside | 0–21% |
| Oleic acid | 0–10% |
| Sodium disilicate monohydrate | 18–33% |
| Sodium citrate dihydrate | 18–33% |
| Sodium stearate | 0–2.5% |
| Sodium perborate monohydrate | 0–13% |
| Tetraacetyl ethylene diamine (TAED) | 0–8% |
| Maleic acid/acrylic acid copolymer | 4–8% |
| Enzymes | 0.0001–0.1% |

11) LIQUID AUTOMATIC DISHWASHING COMPOSITION CONTAINING PROTECTED BLEACH PARTICLES

| | |
|---|---|
| Sodium silicate | 5–10% |
| Tetrapotassium pyrophosphate | 15–25% |
| Sodium triphosphate | 0–2% |
| Potassium carbonate | 4–8% |
| Protected bleach particles, e.g. chlorine | 5–10% |
| Polymeric thickener | 0.7–1.5% |
| Potassium hydroxide | 0–2% |
| Enzymes | 0.0001–0.10% |
| Water | Balance |

11) Automatic dishwashing compositions as described in 1), 2), 3), 4), 6) and 5 10), wherein perborate is replaced by percarbonate.

12) Automatic dishwashing compositions as described in 1)–6) which additionally contain a manganese catalyst. The manganese catalyst may, e.g., be one of the compounds described in "Efficient manganese catalysts for low-temperature bleaching", Nature 369, 1994, pp.637–639.

Furthermore, the first wash lipolytic enzyme of the invention may be used in softening compositions:

The lipolytic enzyme of the invention may be used in fabric softeners, e.g. as described in Surfactant and Consumer Products, Ed. by J. Falbe, 1987, pp 295–296; Tenside Surfactants Detergents, 30 (1993), 6, pp 394–399; JAOCS, Vol. 61 (1984), 2, pp 367–376; EP 517 762; EP 123 400; WO 92/19714; WO 93/19147; U.S. 5,082,578; EP 494 769; EP 544 493; EP 543 562; U.S. 5,235,082; EP 568 297; EP 570 237.

The lipolytic enzyme of the invention may be incorporated in concentrations conventionally employed in detergents. It is at present contemplated that a lipolytic enzyme of the invention may be incorporated in a detergent composition of the invention in an amount corresponding to 0.00001–1 mg (calculated as pure enzyme protein) of lipolytic enzyme per liter of washing liquor.

It is contemplated that the lipolytic enzyme of the present invention may also be useful in, for example, in the baking industry, as a catalyst in organic syntheses (e.g. esterification, transesterification or ester hydrolysis reactions), in the papermaking industry (e.g. for pitch removal), and in the leather, wool and related industries (e.g. for degreasing of animal hides, sheepskin or wool), and for other applications involving degreasing/defatting.

The invention is described in further detail in the following examples which are not in any way intended to limit the scope of the invention as claimed.

MATERIALS AND METHODS

Donor organism: mRNA was isolated from *Humicola insolens* DSM 1800 grown in a maize grits-containing fermentation medium with agitation to ensure sufficient aeration. Mycelia were harvested after 3–5 days' growth, immediately frozen in liquid nitrogen and stored at −80° C.

Yeast strains: The *Saccharomyces cerevisiae* strain used was yNG231 (MAT alpha, leu2, ura 3–52, his4–539, pep4-delta 1, cir +) or JG 169 (MATa; ura 3–52; leu 2–3, 112; his 3–D200; pep 4–1137; prc1::HIS3; prb1:: LEU2; cir+).

Plasmids: The expression plasmid pYES 2.0 (from Invitrogen) was employed.

The Aspergillus expression vector pHD414 was employed. pHD414 is a derivative of the plasmid p775

(described in EP 0 238 023). The construction of pHD414 is further described in WO 93/11249.

Extraction of total RNA was performed with guanidinium thiocyanate followed by ultracentrifugation through a 5.7 M CsCl cushion, and isolation of poly(A)+RNA was carried out by oligo(dT)-cellulose affinity chromatography using the procedures described in WO 94/1 4953.

cDNA synthesis and modification: Double-stranded cDNA was synthesized from 5 µg of poly(A)+RNA by the RNase H method (Gubler & Hoffman 1983, Sambrook et al., 1989) using the hair-pin modification, The procedure is further described in WO 95/02043. After having been treated with mung bean nuclease (Bethesda Research Laboratories), the ds cDNA was made blunt-ended with T4 DNA polymerase (Invitrogen) and the CDNA was ligated to non-palindromic BstX I adapters (1 µg/µl, Invitrogen) in accordance with the manufacturers instructions.

Construction of cDNA libraries: The adapted, ds cDNA was recovered by centrifugation, washed in 70% ethanol and resuspended in 25 ml $H_2O$. Prior to large-scale library ligation, four test ligations were carried out, each using 1 µl ds cDNA (reaction tubes #1 –#3), 2 units of T4 ligase (invitrogen) and 50 ng (tube #1), 100 ng (tube #2) and 200 ng (tubes #3 and #4) Bst XI cleaved yeast expression vector pYES 2.0 (Invitrogen) in a total volume of 10 µl.

Using the optimal conditions a large-scale ligation was set up in 40 µl of ligation buffer. One µl aliquots were transformed into electrocompetent *E. coli* 1061 cells, and the transformed cells were titered and the library plated on LB + ampicillin plates with 5000–7000 colony-forming units (c.f.u.)/plate. To each plate was added 3 ml of medium. The bacteria were scraped off, 1 ml glycerol was added and stored at –80° C. as pools. The remaining 2 ml were used for DNA isolation. For further details reference is made to WO 94/14953.

Construction of yeast libraries: To ensure that all the bacterial clones were tested in yeast, a number of yeast transformants 5 times larger than the number of bacterial clones in the original pools was set as the limit.

One µl aliquots of purified plasmid DNA (100 ng/µl) from individual pools were electroporated (200Ω, 1.5 kV, 25 µF) into 40 µl competent S. cerevisiae JG 169 cells (OD600=1.5 in 500 ml YPD, washed twice in cold de-ionized water, once in cold 1 M sorbitol, resuspended in 0.5 ml 1 M sorbitol (Becker & Guarante, 1991). After addition of 1 ml 1 M cold sorbitol, 80 µl aliquots were plated on SC-URA+glucose to give 250–400 c.f.u./plate and incubated at 30° C. for 3–5 days.

Identification of positive colonies: After 3–5 days of growth, the agar plates were replica plated onto SC-olive oil/brilliant green plates and then incubated for 2–4 days at 30° C. for detection of lipolytic activity. SC-URA-olive oil/brilliant green plates, which are SC-URA +2% glucose +0.6% olive oil +1 % Brilliant Green solution +0.036% polyvinyl alcohol (MW 70,000–100,000 Sigma P-1763 -uracil. After incubation lipolytic enzyme-positive colonies were identified as white colonies with a green halo around.

Cells from enzyme-positive colonies were spread for single colony isolation on agar, and an enzyme-producing single colony was selected for each of the lipolytic enzyme-producing colonies identified.

Characterization of positive clones: The positive clones were obtained as single colonies, the cDNA inserts were amplified directly from the yeast colony using biotinylated polylinker primers, purified by magnetic beads (Dynabead M-280, Dynal) system and characterized individually by sequencing the 5'-end of each cDNA clone using the chain-termination method (Sanger et al., 1977) and the Sequenase system (United States Biochemical).

Isolation of a cDNA gene for expression in Aspergillus: One or more lipolytic enzyme-producing yeast colonies were inoculated into 20 ml YPD broth in a 50 ml glass test tube. The tube was shaken for 2 days at 30° C. The cells were harvested by centrifugation for 10 min. at 3000 rpm.

DNA was isolated according to WO 94/14953 and was dissolved in 50 µl water. The DNA was transformed into *E. coli* as described in WO 94/14953. Plasmid DNA was isolated from *E. coli* using standard procedures, and analyzed by restriction enzyme analysis. The cDNA insert was excised using appropriate restriction enzymes and ligated into an Aspergillus expression vector.

Transformation of *Aspergillus oryzae* or *Aspergillus niger*:

Protoplasts may be prepared as described in WO 95/02043, p. 16, line 21—page 17, line 12.

100 µl of protoplast suspension is mixed with 5–25 µg of the appropriate DNA in 10 µl of STC (1.2 M sorbitol, 10 mM Tris-HCl, pH=7.5, 10 mM $CaCl_2$). Protoplasts are mixed with p3SR2 (an *A. nidulans* amdS gene carrying plasmid). The mixture is left at room temperature for 25 minutes. 0.2 ml of 60% PEG 4000 (BDH 29576), 10 mM $CaCl_2$ and 10 mM Tris-HCl, pH 7.5,is added and carefully mixed (twice), and finally 0.85 ml of the same solution is added and carefully mixed. The mixture is left at room temperature for 25 minutes, spun at 2500 g for 15 minutes and the pellet is resuspended in 2 ml of 1.2 M sorbitol. After one more sedimentation the protoplasts are spread on minimal plates [Cove, Biochem. BiorhVs. Acta 113 (1966) 51–56] containing 1.0 M sucrose, pH 7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Test of *A. oryzae* transformants:

Each of the transformants were inoculated in 1 0 ml YPM and propagated. After 2–5 days of incubation at 30° C., 10 ml supernatant was removed. The lipolytic activity was identified by applying 10 µl supernatant to 4 mm diameter holes punched out in agar plates containing 0.1 M Tris pH 9, 0.1 M $CaCl_2$, 1% Triton X-100, 0,5% olive oil. Lipolytic activity is indicated by the formation of a turbid halo.

Hybridization conditions (to be used in evaluating property ii) of the DNA construct of the invention): Suitable conditions for determining hybridization between an oligonucleotide probe and an "analogous" DNA sequence involve presoaking of the filter containing the DNA sequences to hybridize in 5×SSC, and prehybridizing the sequences for 1 h at~50° C. in a solution of 5×SSC, 5xDenhardt's solution, 50 mM sodium phosphate, pH 6.8, and 50 µg of denatured sonicated calf thymus DNA, followed by hybridization in the same solution supplemented with 50 µCi $^{32}$P-dCTP labelled probe for 18 h at~50° C. followed by washing three times in 2×SSC, 0.2% sodium dodecyl sulfate (SDS) at 50° C. for 30 minutes.

A suitable oligonucleotide probe to be used in the hybridization may be prepared on the basis of the DNA sequence shown in SEQ ID No. 1 or a suitable subsequence of said sequence (e.g. a 20 nucleotide fragment thereof). Alternatively, a suitable oligonucleotide probe may be prepared on the basis of the amino acid sequence shown in SEQ ID No. 2.

Immunological cross-reactivity: Antibodies to be used in determining immunological cross-reactivity may be prepared by use of a purified lipolytic enzyme. More specifically, antiserum against the enzyme of the invention may be raised by immunizing rabbits (or other rodents) according to the procedure described by N. Axelsen et al. in: *A Manual of Quantitative Immunoelectrophoresis*, Blackwell Scientific Publications, 1973, Chapter 23, or A. Johnstone and R. Thorpe, *Immunochemistry in Practice*, Blackwell Scientific Publications, 1982 (more specifically pp. 27–31). Purified immunoglobulins may be obtained from the antisera, for example by salt precipitation [$(NH_4)_2SO_4$], followed by dialysis and ion exchange chromatography, e.g. on DEAE-Sephadex™. Immunochemical characterization of proteins may be done either by Outcherlony double-diffusion analysis (O. Ouchterlony in: *Handbook of Experimental Immunology* (D. M. Weir, Ed.), Blackwell Scientific Publications, 1967, pp. 655–706) by crossed Immunoelectrophoresis (N. Axelsen et al., supra, Chapters 3 and 4), or by rocket immunoelectrophoresis (N. Axelsen et al., supra, Chapter 2).

Media

YPD: 10 g yeast extract, 20 g peptone, $H_2O$ to 900 ml. Autoclaved, 100 ml 20% glucose (sterile filtered) added.

YPM: 10 g yeast extract, 20 g peptone, $H_2O$ to 900 ml. Autoclaved, 100 ml 20% maltodextrin (sterile filtered) added.

10×Basal salt: 66.8 g yeast nitrogen base, 100 g succinic acid, 60 g NaOH, $H_2O$ ad 1000 ml, sterile filtered.

SC-URA: 90 ml 10×Basal salt, 22.5 ml 20% casamino acids, 9 ml 1% tryptophan, $H_2O$ ad 806 ml, autoclaved, 3.6 ml 5% threonine and 90 ml 20% glucose or 20% galactose added.

SC-URA agar: SC-URA, 20 g/l agar added.

Olive Oil: Sigma 0-1500.

Brilliant Green solution: 4 mg/i of Brilliant Green (Sigma B-6756) in water.

EXAMPLE 1

An *E. coli* library from *H. insolens* DSM 1800 consisting of approx. $10^6$ individual clones in 50 pools was constructed.

DNA was isolated from 20 individual clones from the library and subjected to analysis for cDNA insertion. The insertion frequency was found to be >90% and the average insert size was approximately 1400bp. DNA from some of the pools was transformed into yeast, and 50–100 plates containing 200–500 yeast colonies were obtained from each pool.

More than 70 positive colonies were identified and isolated on agar plates. cDNA inserts were amplified directly from the yeast colony and characterized as described in the Materials and Methods section above. The cDNA sequence encoding the lipolytic enzyme is shown in SEQ ID No. 1.

Subsequently, the cDNA encoding the lipolytic enzyme was isolated for expression in Aspergillus as described above and transformed into *E. coli* using standard procedures. Two *E. coli* colonies were isolated from each of the transformations and analyzed with the restriction enzymes Hindlll and Xbal which excised the DNA insert. DNA from one of these clones was retransformed into yeast strain JG169.

EXAMPLE 2

In order to express the gene in Aspergillus, cDNA is isolated and digested with Hindlll/Xbal, subjected to size fractionation on a gel and purification, and subsequently ligated to pHD414, resulting in the plasmid pA2L79. After amplification in *E. coli*, the plasmid is transformed into *A. oryzae* or *A. niger* according to the general procedure described above.

Test of *A. oryzae* transformants

Each of the transformants was tested for lipolytic activity as described above. Some of the transformants had lipolytic activity which was significantly higher than the *Aspergillus oryzae* background. This demonstrates efficient expression of lipolytic enzyme in *Aspergillus oryzae*.

The transformant with highest lipolytic activity was selected and inoculated in a 500 ml shake flask with YPM medium. After 3–5 days of fermentation with sufficient agitation to ensure good aeration, the culture broths were centrifuged for 10 minutes at 2000 g, and the supernatant was recovered and analyzed.

The lipolytic activity in the supernatants was identified as described above.

Batch fermentation

Batch fermentation was performed in a medium comprising maltose syrup as a carbon source, urea as a nitrogen source and yeast extract. The batch fermentation was performed by innoculating a shake flask culture of *A. oryzae* host cells in question into a medium comprising 3.0% of the carbon source and 0.4% of the nitrogen source. After 24 hours of cultivation at pH 7.0 and 34° C. the fermentation was terminated, after which the enzymes could be recovered by centrifugation, ultrafiltration, clear filtration and germ filtration.

EXAMPLE 3

Purification and characterization of a *H. insolens* lipolytic enzyme

The batch fermentation supernatant was centrifuged and the precipitate containing cell debris discarded. The supernatant was adjusted with solid ammonium sulphate to 60% saturation and allowed to stand overnight. Precipitate containing cutinase activity was separated by centrifugation. Ammonium sulphate precipitate was dissolved in water and adjusted to pH 6 with dilute acetic acid. The sample containing lipolytic activity was passed on Bacitracin agarose column to get rid of alkaline protease activity present in A. oryzae. Lipolytic activity which does not bind to Bacitracin agarose was collected as effluent.

The pool containing activity was adjusted to pH 5.8 and ionic strength was adjusted to 2 Milli Siemens. The sample was applied on a cation exchanger SP-Sepharose™high-performance Pharmacia™column which was equilibrated with 25 mM sodium acetate buffer, pH 5.8.

The bound activity was eluted with linear salt gradient using the same buffer.

The molecular weight of the purified protein was determined using SDS-PAGE PHAST 8–25% gradient gels (PHAST system™, Pharmacia). The molecular weight was estimated to 20–21 kD.

The isoelectric point of the protein was determined using Ampholine™ PAGE plates, pH 3.5–9.5 (Pharmacia LKB) in accordance with the manufacturer's instructions, pI was found to be 8.

The lipolytic enzyme was found to be inhibited by phenyl methyl sulphinyl fluoride, suggesting a solvent-accessible active site and thus esterase activity.

Assay for lipase activity and specific activity of the lipolytic enzyme

Lipase activity was determined using a substrate prepared by emulsifying glycerol tributyrate (MERCK) using gum arabic as emulsifier.

Lipase activity was assayed at pH 7 using a pH-stat method (employing a Radiometer VTT Titrator Tm). One unit of lipase activity (LU) is defined as the amount needed to liberate one micromole of fatty acid per minute.

Specific activity at pH 7 was determined to be at least about 1200 LU/mg.

Substrate specificity: To compare the lipolytic activity of the *H. insolens* lipolytic enzyme of the invention (having the amino acid sequence shown in SEQ ID No. 2) towards a long-chain substrate (olive oil) and a short-chain substrate (glycerol tributyrate), two assays were carried out at pH 9:

1) Sigma olive oil substrate assay using Sigma lipase substrate emulsion (Sigma catalogue No. 800-1), and
2) an assay with tributyrin (glycerol tributyrate) as substrate, using gum arabic as emulsifier. Both the assays were carried out using a pH-stat method at pH 9. At pH 9, the activity of the lipolytic enzyme was around 500 Sigma lipase unit/OD280 and around 1500 LU/OD280 in assays 1 and 2, respectively, suggesting that the lipolytic enzyme has better activity against short chain substrates such as tributyrin.

pH optimum of the *H. insolens* lipolytic enzyme

The lipolytic activity of the enzyme at different pH values was investigated with glycerol tributyrate as substrate and gum arabic as emulsifier, using the pH-stat method. The activity of the enzyme as a function of pH (pH 6, 7, 8, 9, 10, respectively) is shown in FIG. 1. The pH optimum appears to be about 8, with a high percentage of the maximum activity still being retained at pH 10.

N-terminal sequencing

The *H. insolens* DSM 1800 lipolytic enzyme of the invention was finally purified using reversed phase HPLC. The N-terminal amino acid sequence of the enzyme was determined for 27 residues using an Applied Biosystems sequencer. The resulting sequence is shown in SEQ ID No. 3, in which Xaa designates an unassigned residue that almost certainly is a cysteine residue. In position 12, both Gly and Ala were found in equal amounts.

EXAMPLE 4

Performance of the *H. insolens* DSM 1800 lipolytic enzyme of the invention in an assay for assessing "First Wash" lipolytic effect The textile/laundry washing performance of the lipolytic enzyme of the invention was tested in a one-cycle washing trial carried out in a thermostatted Terg-O-Tometer (TOM) followed by line-drying.

The experimental conditions were as follows:

Washing liquor: 1000 ml per beaker

Swatches: 7 cotton swatches (9×9 cm) per beaker.

Stain: Lard colored with Sudan Red (Sigma) (0.75 mg Sudan Red/g of lard). 50 µl of colored lard heated to 70° C. was applied to the center of each swatch. The swatches were then heated in an oven for 25 minutes at 75° C. and stored overnight at room temperature prior to the first wash.

Water hardness: 3.2 mM $Ca^{2+}$/$Mg^2$, (in a ratio of 5:1)

Detergent: 5 g/l of a standard, commercial European compact powder detergent 5 (Ariel™Futur). No pH adjustment.

Concentration of lipolytic enzyme: O LU/I (control) and 12500 LU/I

Wash Time: 20 minutes

Wash temperature: 30° C.

Rinse: 15 minutes in running tap water

Drying: Overnight at room temperature (approx. 20° C., 30–40% RH).

Evaluation: After washing, rinsing and drying the swatches, residual fatty matter was extracted with petroleum ether in a Soxhlet extraction apparatus. The solvent was distilled off and the amount of residual fatty material extracted from the swatches was determined by weighing.

Results: relative to the amount of residual fatty material in swatches washed in the enzyme-free washing liquor, washing of swatches in the enzyme-containing washing liquor resulted in removal of 16% of the fatty material.

It is apparent from these results that the lipolytic enzyme in question (a lipolytic enzyme of the invention) is capable of excellent "first-wash" removal of lipid in textile washing.

EXAMPLE 5

Substrate affinity of the *H. insolens* DSM 1800 lipolytic enzyme of the invention The following procedure is designed to assess the ability of a lipolytic enzyme to accumulate on/in a lipid substrate phase (in this case olive oil) which is in contact with a buffered, alkaline aqueous phase containing the enzyme, in the presence of a non-ionic surfactant. In this example, the substrate affinity of the above-mentioned lipolytic enzyme of the invention was compared with that of the commercial lipolytic enzyme Lipolase™ (available from Novo Nordisk A/S, Bagsvaerd, Denmark).

Procedure

1. A 5 ml aliquot of buffer solutions (100 mM glycine, pH 9.0) was placed in each of two identical, sealable, 20 ml vials;

2. The chosen enzyme is added to both vials to give a concentration in the range of 5–10 LU/mi (same concentration in both vials);

3. 5 ml of olive oil is added to one vial ("sample" vial), and both vials are shaken vigorously and incubated for 24 hours at 4° C.;

4. residual lipolytic activity (denoted Y below; in LU/ml) in the aqueous phases in the "sample" (s) vial and the "reference" (r) vial, respectively, is determined.

The ratio $Y_s/Y_r$ gives a measure of the substrate affinity of the enzyme in question.

Results: The results for the lipolytic enzyme of the invention and for Lipolase™, respectively, are shown in the following table.

| Enzyme | $Y_S/Y_r$ × 100(%) |
|---|---|
| Invention | 2 |
| Lipolase ™ | 99 |

It is apparent from the above that the enzyme according to the invention exhibits very high affinity for olive oil.

EXAMPLE 6

Lipolytic activity of the *H. insolens* DSM 1800 lipolytic enzyme of the invention in a mixed monolayer containing an alcohol ethoxylate A mixed monolayer was prepared from a diglyceride (dicaproin) and a mono-component alcohol ethoxylate (heptaethylene glycol monooctadecyl ether) spread on a aqueous phase (10 mM glycine, pH 10.0, 0.1 mM EDTA; temperature 25° C.) using a KSV-5000 monolayer apparatus (KSV Instruments, Finland). The surface pressure was adjusted to the desired value (in this case 30 mN/m) and the chosen enzyme (10 LU) was injected into the aqueous phase.

Lipolytic action manifests itself through the speed with which a mobile barrier compressing the monolayer has to be moved in order to maintain a constant surface pressure as water-insoluble substrate molecules are hydrolyzed to give more water-soluble products.

Using this procedure, a particular lipolytic enzyme is characterized by a parameter β which indicates the final area percentage of substrate remaining unhydrolyzed by the enzyme as lipolytic activity ceases.

In this example, the *H. insolens* DSM 1800 enzyme of the invention was compared with the commercial enzyme Lipolase™

Results: the results are summarized in the table below.

| Enzyme | β (%) |
|---|---|
| Invention | 37 |
| Lipolase ™ | 57 |

It is apparent from the latter results that the lipolytic enzyme of the invention performs very well in lipid hydrolysis in the presence of an alcohol ethoxylate (i.e. a non-ionic surfactant).

REFERENCES

Becker, D. M. & Guarante, L. 1991. Methods Enzymol. 194: 182–187.

Gubler, U. & Hoffman, B. J. 1983. Gene 25: 263–269.

Sambrook, J., Fritsch, E. F. & Maniatis, T. 1989. Molecular Cloning: A Laboratory Manual. Cold Spring Harbor Lab., Cold Spring Harbor, N.Y.

Sanger, F., Nicklen, S. & Coulson, A. R. 1977. Proc. Natl. Acad. Scd. U. S. A. 74: 5463–5467.

What is claimed:

1. A DNA sequence encoding an enzyme exhibiting lipolytic activity, wherein the DNA sequence is one of:

(a) the DNA sequence of SEQ ID NO:1;

(b) a DNA sequence encoding a lipase having the amino acid sequence of SEQ ID NO:2; or (c) the DNA sequence isolated from *Saccharomyces cerevisiae* DSM.

2. The DNA of claim 1, wherein the DNA sequence is obtained from a microorganism.

3. The DNA sequence of claim 2, wherein the DNA sequence is obtained from a filamentous fungus or a yeast.

4. The DNA sequence of claim 3, wherein the DNA sequence is obtained from a strain of Thielavia, Chaetomium, Gelasinospora, Neurospora, Podospora, Sordaria or Humicola.

5. The DNA sequence of claim 4, wherein the DNA sequence is obtained from a strain of Chaetomium or Humicola.

6. The DNA sequence of claim 5, wherein the DNA sequence is isolated from a DNA library prepared from *H. insolens* DSM 1800.

7. A recombinant expression vector comprising a DNA sequence of claim 1.

8. A cell transformed with the DNA sequence of claim 1.

9. The transformed cell of claim 8, wherein said cell is a eukaryotic cell.

10. The transformed cell of claim 9, wherein the cell belongs to a strain of Aspergillus or Trichoderma.

11. A method of producing an enzyme exhibiting lipolytic activity, the method comprising culturing the transformed cell of claim 8 under conditions conducive to the production of the enzyme, and recovering the enzyme from the culture.

* * * * *